United States Patent [19]

Hollister

[11] Patent Number: 5,133,758
[45] Date of Patent: Jul. 28, 1992

[54] TOTAL KNEE ENDOPROSTHESIS WITH FIXED FLEXION-EXTENSION AXIS OF ROTATION

[75] Inventor: Anne Hollister, Torrance, Calif.

[73] Assignee: Research and Education Institute, Inc. Harbor-UCLA Medical Center, Torrance, Calif.

[21] Appl. No.: 760,115

[22] Filed: Sep. 16, 1991

[51] Int. Cl.⁵ ............................................. A61F 2/38
[52] U.S. Cl. ...................................................... 623/20
[58] Field of Search .................................... 623/18, 20

[56] References Cited

U.S. PATENT DOCUMENTS

| | | | |
|---|---|---|---|
| 4,085,466 | 4/1978 | Goodfellow et al. | 623/20 |
| 4,261,064 | 4/1981 | Helfet | 623/20 X |
| 4,301,553 | 11/1981 | Noiles | 623/20 |
| 5,047,057 | 9/1991 | Lawes | 623/20 |
| 5,071,438 | 12/1991 | Jones et al. | 623/20 |

FOREIGN PATENT DOCUMENTS

0069683 1/1983 European Pat. Off. .............. 623/20

Primary Examiner—Randall L. Green
Assistant Examiner—D. Willse
Attorney, Agent, or Firm—Drucker & Sommers

[57] ABSTRACT

The invention is a total knee endoprosthesis with a fixed flexion-extension axis throughout all degrees of flexion and extension of the knee. The endoprosthesis has a femoral component with spaced apart medial and lateral condyle portions which slidably seat on a tibial implant portion. The fixed flexion-extension axis is directed inferiorly and posteriorly from the medial condyle portion to the lateral condyle portion and is offset from both the transverse and coronal planes equally by 3.0 to 3.8 degrees. A longitudinal axis through the tibia allows the tibia to rotate nonorthogonally and anteriorly of the flexion-extension axis. A patellar groove which is perpendicular to the flexion-extension axis. In the patellar groove slides an optional patellar component or the natural patella.

20 Claims, 7 Drawing Sheets

TOTAL KNEE ENDOPROSTHESIS WITH FIXED FLEXION-EXTENSION AXIS OF ROTATION

BACKGROUND OF THE INVENTION

1. Field of the Invention

This invention pertains to the field of total knee endoprosthesis devices.

2. Description of the Prior Art

The human knee joint is one of the most stressed joints of the human body. In normal activities such as walking, running, kneeling, and climbing stairs, the load put on the knee joint can easily exceed five times the weight of the body, and for those who engage in more strenuous activities, can be much higher. Various forms of arthritis affect approximately 10 percent of the world's population. A significant number of those suffering from arthritis experience severe deterioration and deformity of joints such as the knee joint. Those who have experienced knee trauma are particularly susceptible to disabling arthritis. Approximately 140,000 patients are operated on each year in the United States alone for total knee replacement. Many more individuals suffering from knee joint problems would be candidates for total knee replacements if there existed knee endoprosthesis which more closely mimic the anatomical knee.

Knee joint prostheses can be classified into two basic types. The first type, referred to as "stabilized" prothesis, has hinge or ball and socket type joints used as substitutes for the anatomical knee joint. In this type of joint, the movement of the joint is constrained by a hinge pin or ball and socket. The stabilized prothesis is useful where little reliance can be placed on the surrounding soft tissues (i.e. tendons and ligaments) to stabilize the joint. Unlike the anatomical knee joint, these joints allow little, if any, anterior-posterior translation, lateral angulation, or rotation. For this reason, such joints are undesirable.

The second type of knee joint protheses are the so-called "condylar surface" protheses. In these types of protheses, the corresponding bearing surfaces on the femur and tibia are replaced by analogously shaped and positioned prosthetic bearing surfaces. Condylar surface prothesis joints rely upon the surrounding tendons and ligaments to hold the femoral and tibial portions of the joint, which are not directly connected to each other, together and to impart stability to the joint during movement. These types of joints are relatively compact and light, afford substantial rotational and translational freedom of movement, and require relatively minor resection of the natural bone and disturbances of the surrounding soft tissues during implantation. Examples of these types of prosthetic joints are disclosed in U.S. Pat. No. 3,798,679 to Ewald; U.S. Pat. No. 4,064,568 to Grundei, et al.; U.S. Pat. No. 4,224,696 to Murray, et al.; U.S. Pat. No. 4,673,408 to Grobbelaar; U.S. Pat. No. 4,714,472 to Averill, et al.; U.S. Pat. No. 4,770,663 to Hanslik, et al.; U.S. Pat. No. 4,822,365 to Walker, et al.; U.S. Pat. No. 4,822,366 to Bolesky; U.S. Pat. No. 4,944,756 to Kenna; U.S. Pat. No. 4,959,071 to Brown, et al.; and U.S. Pat. No. 4,985,037 to Petersen.

However, regardless of the type of artificial knee joint design, the medical community and designers of total knee endoprosthetic devices have long believed that the movement of the knee joint in flexion and extension does not take place in a simple hinge-like manner. Rather, it has heretofore been universally accepted that the flexion and extension knee movement includes displacement and rotation, so that the same parts of a first articulating surface (the condyles of the femur) are not always in contact with the same part of a second corresponding articulating surface (the tibial plateau) with the axis of motion not being fixed. Thus, it has been believed that the knee acts not as a simple hinge joint, but turns in extension and flexion through an infinite succession of uniquely placed centers of rotation, each center acting at a particular relative orientation of the femur and the tibia. See for example, "The Surgical Replacement of the Human Knee Joint," by David A. Sonstegard, et al., *Scientific American*, January, 1978, Vol. 238, No. 1.

U.S. Pat. No. 4,822,365 to Walker, et al. discusses the historical development of knee protheses design and provides general background in this area. Through the years, improvements have been made in the materials used to manufacture knee protheses and in the designs based on the belief that the flexion-extension axis is not fixed. However, as will be discussed in greater detail below, the inventor has discovered that in the anatomical knee, the flexion-extension axis is actually fixed. Because the designs of prior art total knee endoprostheses devices are based upon the incorrect basic assumption that the flexion-extension axis is non-fixed and has a constantly changing axis of rotation, the prior art prosthetic knee joints remain far inferior to the natural human knee in the degree of motion possible and the strains and stress put on these artificial knee joints. Although the artificial knee joints of today are far better than those of years past, they still suffer from failure by fracturing and detachment from the bones to which they are attached. These problems are in turn largely caused by the unnatural stresses and strains put on the prosthetic knee as a result of their designs.

SUMMARY OF THE INVENTION

The present invention signals a revolutionary departure from prior art total knee endoprostheses designs based on the incorrect belief that the flexion-extension axis of rotation is non-fixed and constantly changing. The applicant has discovered that the natural anatomical human knee actually has a fixed flexion-extension axis of rotation that does not change depending upon the orientation of the tibia to the femur through flexion and extension. Before summarizing the features of the invention, the applicant describes below what she believes to be the true anatomy and function of the normal anatomical knee.

In the natural human knee, this fixed axis of flexion-extension, (hereinafter "FE") axis is directed from anterior-superior on the medial condyle of the distal femur to posterior-inferior on the lateral condyle and passes through the origins of the medial and lateral collateral ligaments. The FE axis is superior to the crossing point of the cruciate ligaments. The fixed FE axis is offset from the transverse and coronal planes equally by approximately 3.0 to 3.8 degrees. The longitudinal axis of rotation (LR) of the tibia is likewise a fixed axis and is anterior and not perpendicular to the FE axis. The offset of the FE axis from the transverse and coronal planes explains the observed valgus external rotation with extension for the knee and the varus internal rotation with flexion of the knee. When motion occurs about the fixed FE axis (by flexion-extension of the knee) and LR axis (by turning of the foot), which are non-orthogonal axes, the motion is pure rotation about these axes. The FE axis passes through the origins of the medial collateral ligaments (MCL) and lateral collateral ligaments (LCL) on the sides of the distal femur and is superior to the intersection of the cruciate ligaments. The LR axis passes through the insertion of the anterior cruciate ligament (ACL) on the tibial plateau and is directed postero-medially in the proximity of the insertion of the posterior cruciate ligament (PCL) at the femoral notch. The patellar groove is perpendicular to the FE axis its entire length. When the condyles are viewed end on perpendicular to the FE axis, the posterior and distal portions of the medial and lateral femoral condyles are superimposed and are circular in shape. As the tibia and fibia rotate relative to each other, the FE axis remains unchanged. The lateral condyle has a smaller radius of curvature than the medial condyle and the lateral joint surface is thus closer to the FE axis, thus accounting for the fixed FE axis. The medial and lateral surfaces of each condyle are rounded off to allow the tibia to move about the LR axis relative to the FE axis.

The LR axis is anterior and not perpendicular to the FE axis. It is fixed in the tibia and moves about the FE axis. The LR axis passes near the anterior cruciate ligament insertion on the tibia and is directed postero-medially near the posterior cruciate insertion on the femur.

As has been explained, classically, joint motion has been considered to occur about axes which lie in the anatomic planes, with separate perpendicular axes for FE, LR, and abduction-adduction (AA). However, it is now known that the FE axis is offset from the coronal and transverse planes, and that the LR axis does not lie in the sagittal plane. The FE and LR axes are furthermore nonorthogonal. Since the FE and LR axes of rotation do not lie in the anatomical planes, the joint motions about the fixed FE and LR axes account for the observed three movements of FE, LR, and AA. Motion about each axis includes varus-valgus flexion-extension and internal-external rotation. The major component of motion about the FE axis is flexion and extension, but conjoint varus and internal rotation occur with flexion because the axis is not perpendicular to the sagittal plane.

The relationship of the cruciates to the two fixed axes suggests their isometry in the physiologic range of knee motion. As has been noted, the FE axis passes through the origins of the MCL and LCL on the distal end of the femur. The anatomy of the LCL and MCL are more complex than the cruciate ligaments since they are dynamically stabilized and the LCL crosses the tibio-fibular joint as well as the knee.

The observed fixed non-orthogonal axes FE and LR explain the shape of the condyles, the location of the ligaments, and the obligatory tibial varus and internal rotation that occur with flexion. Since prior art prostheses, braces, models for gait, calculations of forces, and reconstructive surgery are based on the incorrect belief of a constantly changing horizontal FE axis, the implications for the design of knee endoprostheses are profound, and the total knee endoprosthesis of this invention with a fixed flexion-extension axis is now briefly described.

The knee prosthesis of the present invention is designed to closely mimic the natural human knee and comprises in combination a femoral component and a tibial plateau component. The femoral component has a medial condyle portion and a lateral condyle portion, the two condyle portions being separated by a patellar groove at its anterior face and by a space distally and proximally. The radii of curvature of the posterior part of the two condyles are circular, when viewed perpendicularly to the FE axis, through a sweep of approximately 135 degrees and the medial condyle has a larger radius of curvature than the lateral condyles portions such that the FE axis passing through the two centers of curvature is directed 3.0 to 3.8 degrees posteriorly and inferiorly from the medial condyle portion to the lateral condyle portion. The FE axis is offset by an equal angle from both the transverse and coronal planes. The patellar groove is perpendicular to the FE axis. The FE axis can be placed as passing through the center of the medial condyle portion, through the sagittal plane, at a position that is 35 percent ($\pm 5$ percent) of the distance from the posterior-most portion of the medial condyle portion to the anterior projection of the femoral shaft and lies on the posterior side. From that point, the FE axis is directed by an angle of 3 to 3.8 degrees equally posteriorly and inferiorly from the medial condyle portion to the lateral condyle portion.

The tibial plateau component has a top plateau surface with lateral and medial concavities separated by a raised eminence which is higher posteriorly than anteriorly. The medial concavity is larger and deeper than the lateral concavity to slidably engage with the corresponding medial and lateral condyle portions of the femoral component. Under the bottom of the top plateau surface is a keel for fixation to the top of the tibia bone.

When the prosthetic knee recipient is standing and the prosthetic knee is in extension, the distal most portions of the medial and lateral condyle portions seat in the transverse (horizontal) plane with the tibial plateau. The tibial plateau component is attached to the tibia bone such that the LR axis is anterior and not perpendicular to the FE axis. It is fixed in the tibia and moves about the FE axis. As with the natural anatomical human knee, the LR axis passes near the anterior cruciate ligament insertion on the tibia and is directed postero-medially near the posterior cruciate insertion of the femur.

These and other features of the invention will be more clearly understood by reference to the following detailed description, the appended claims, and to the several views illustrated in the attached drawings.

BRIEF DESCRIPTION OF THE DRAWINGS

In describing the invention, reference will be made to the accompanying drawings wherein.

DETAILED DESCRIPTION OF THE PREFERRED EMBODIMENT

Figure 1:
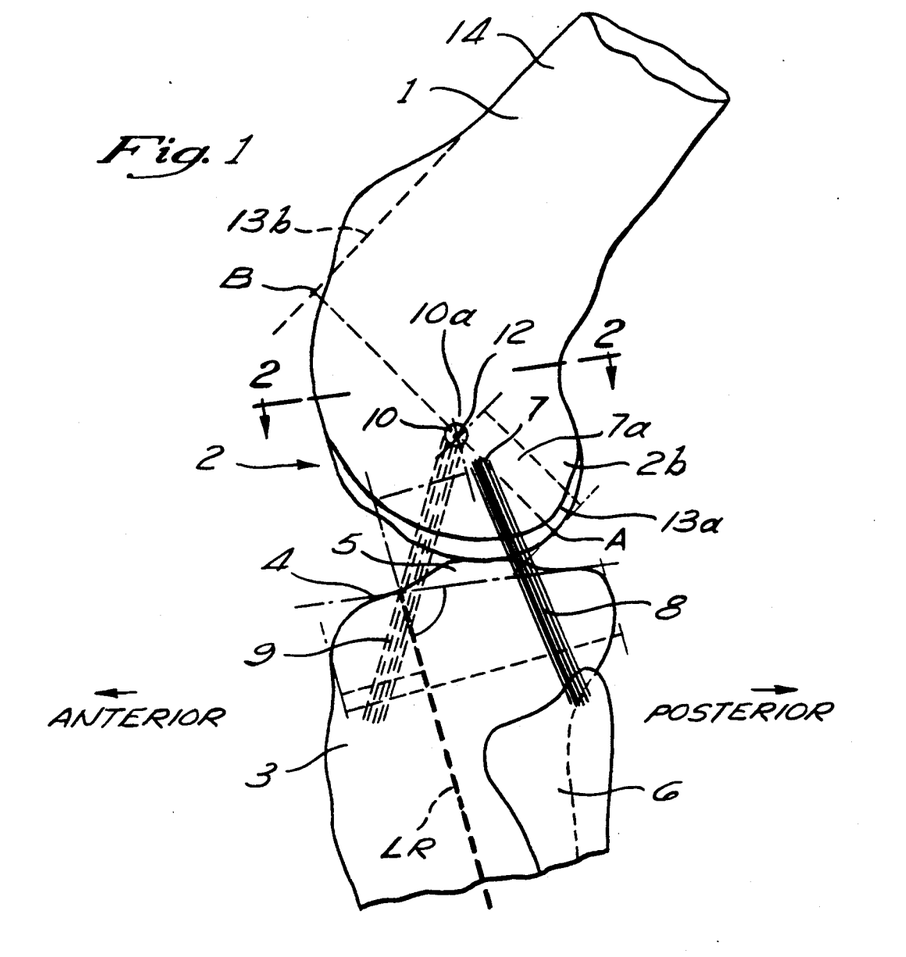
FIG. 1 is a schematic, side-elevational view of the left anatomical human knee through the sagittal plane, as viewed from the lateral side showing the femur, tibia, fibula, LR axis, and the lateral and medial collateral ligaments.
Figure 2:
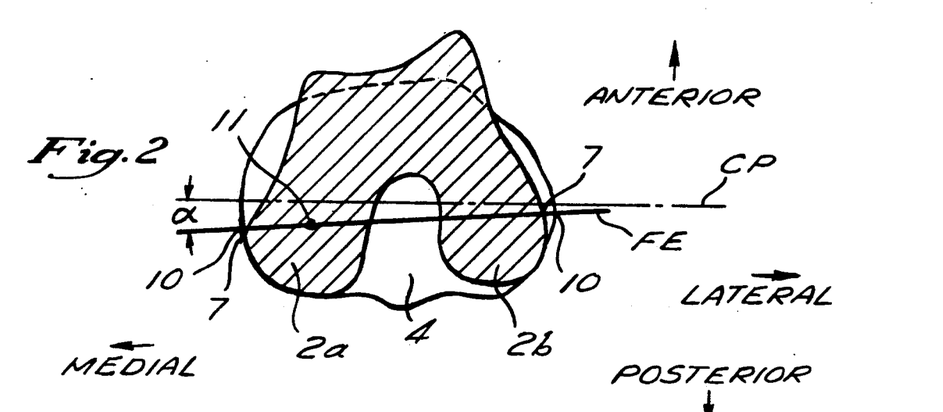
FIG. 2 is a cross-sectional view of the knee of FIG. 1 through the transverse plane showing the offset of the FE axis from the coronal plane.
Figure 3:
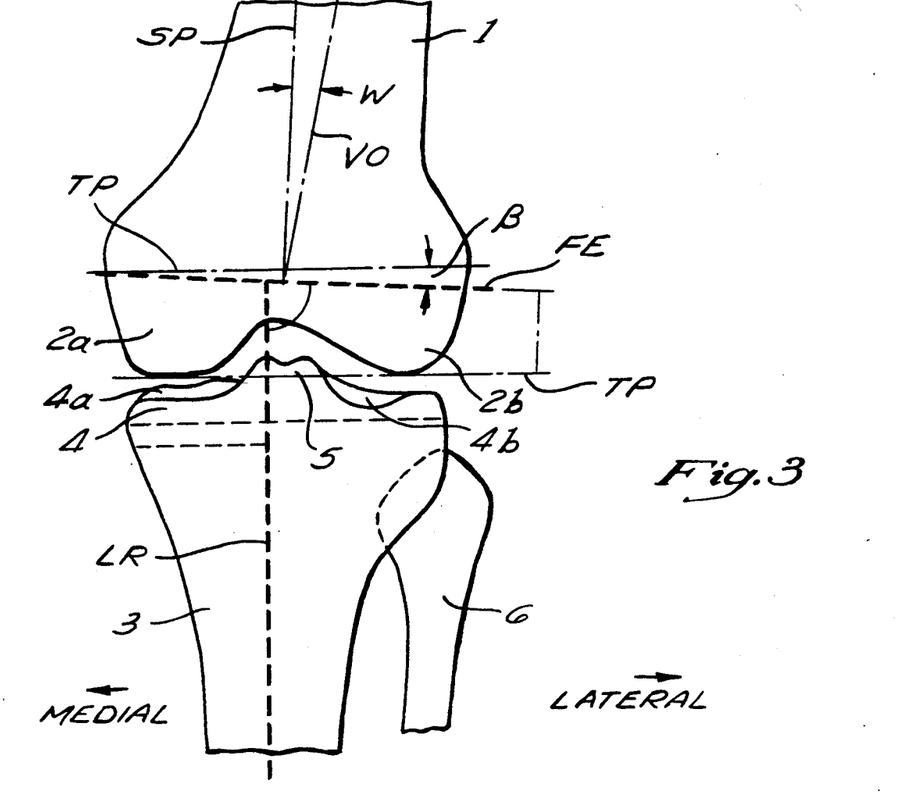
FIG. 3 is an schematic anterior view of the left human knee of FIGS. 1 and 2 showing the nonorthogonal offset of the FE and LR axes and the offset of the FE axis from the transverse plane.

FIGS. 1-3 illustrate, schematically, the anatomy and the orientation of the flexion-extension (FE) axis and the longitudinal rotation axis (LR) in the anatomical human knee. The femur bone 1 has a medial condyle 2a and a lateral condyle 2b at its distal end. As best shown in FIG. 3, the tibia bone 3 terminates at its proximal end with a tibular plateau 4 having a medial and lateral concavity 4a and 4b to seat within the two medial and lateral condyles 2a and 2b, respectively. Dividing the tibial plateau 4 is a raised eminence 5. The fibula bone 6 is below the tibular plateau 4. The origin 7 of the lateral condyle ligament (LCL) 8 is connected to the lateral epicondyle surface 7a. Shown in phantom lines is the medial condyle ligament (MCL) 9, which connects at its origin 10 to the medial epicondyle surface 10a. The flexion-extension axis FE passes through the origins 7 and 10 of the lateral and medial condyle ligaments 8 and 9. The FE axis is offset posteriorly and inferiorly from medial to lateral by an angle ranging from 3.0 to 3.8 degrees equally from both the transverse plane TP and coronal plane CP, as shown, schematically, in FIGS. 2 and 4. The patellar groove (not shown) runs perpendicular to the FE axis.

The above-described position and orientation of the FE axis also corresponds to an orientation in which the FE axis passes through a point 11 in the medial condyle 2a that is approximately 35±5 percent of the distance AB, the distance AB being measured from the posterior-most point A, on the medial condyle 2a to (lying on solid line 13a) perpendicularly to point B lying on the anterior projection of the femoral shaft 13 (the downward projection of the anterior-most line of the femur bone 14 toward the condyles, the projection line being identified by dotted line 13b). The orientation of line AB is such that it intersects the FE axis at point 11. From point 11, the FE axis is directed posteriorly and inferiorly to the lateral condyle 2b by an angle ranging from 3.0 to 3.8 degrees equally from both the transverse plane TP and the coronal plane CP. FIG. 2 best shows the offset of the FE axis by an angle α of 3.0 to 3.8 degrees from the coronal plane CP.

As best shown in FIG. 3, the FE axis is offset by an angle β of 3.0 to 3.8 degrees from the medial condyle 2a to the lateral condyle 2b from the transverse plane TP. The center of the femur VO is offset from the sagittal plane SP by an angle w, typically in the range of 3 to 7 degrees, depending upon the individual.

The fixed offset of the FE axis of the femoral and tibial prothesis components from both the transverse plane TP and coronal plane CP, the circularity of the posterior and distal portions of the medial and lateral condyles about the FE axis, and the position and orientation of the FE axis are among the major features of the invention claimed herein.

Figure 4:
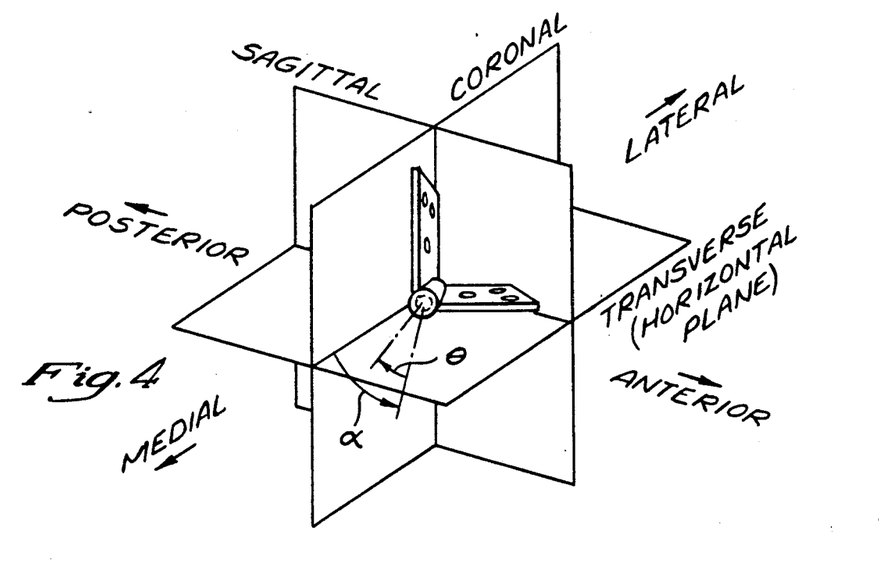
FIG. 4 is a perspective view showing the offset of the FE axis from both the transverse and coronal planes, shown for sake of simplicity as a simple hinge.

FIG. 4 is a diagrammatic representation of the offset of an ordinary hinge, showing the three anatomical planes and its orientation. The hinge of Figure shows the orientation of the FE axis in the anatomical knee and in the total knee prosthesis of the invention, features of which are depicted in FIGS. 5-13 and described herein.

Figure 5:
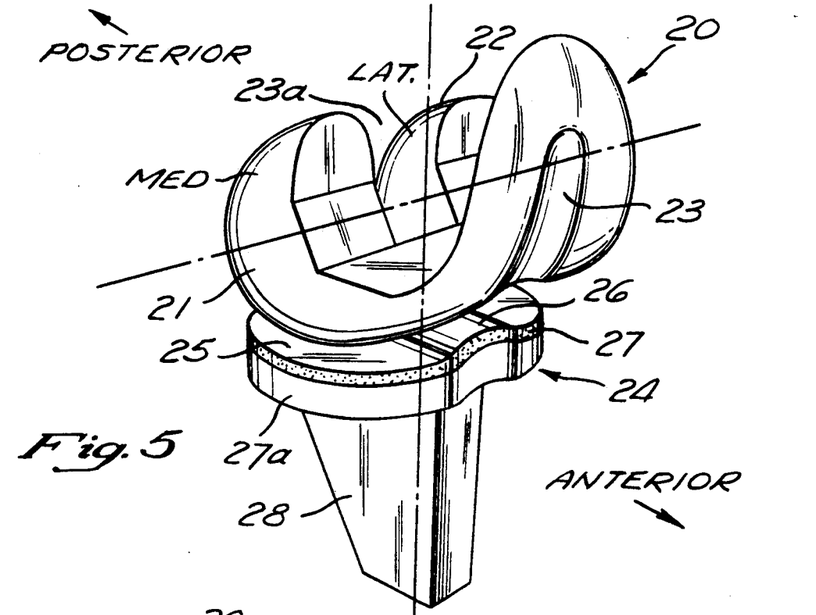
FIG. 5 is an anterior perspective view of the total knee endoprosthesis of the invention.
Figure 6:
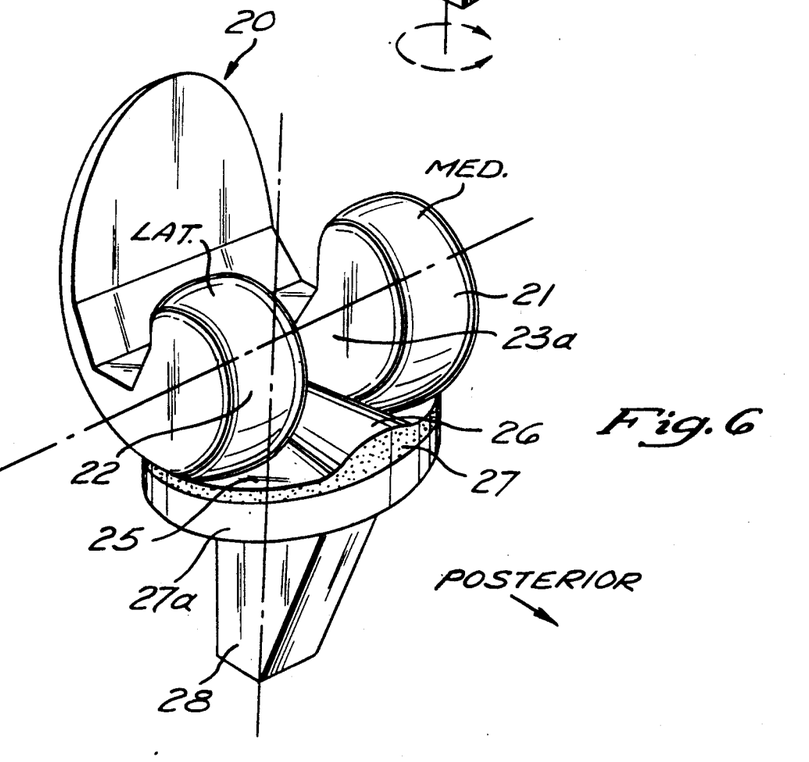
FIG. 6 is a posterior perspective view of the total knee endoprosthesis of FIG. 5.

FIGS. 5 and 6 are a front and rear view, respectively, of a total knee prosthesis 19 for the left knee in the extension orientation. The femoral component 20 has a medial condyle portion 21 and a lateral condyle portion 22. Originating from the anterior side of the femoral component 20 is a patellar groove 23 which wraps around to the posterior portion of the femoral component to define a space 23a between the medial and lateral condyle portions 21 and 22. The tibial component 24 has a plateau 25 with a ridge shaped eminence 26 between two concavities on the tibial plateau within which the condyles seat (shown in FIGS. 8 and 9). Ideally, the plateau 25 will have an upper portion 27 made of a low friction material, such as ultra-high density polyethylene, attached to a lower metallic part 27a. The low friction upper portion 27 is desirably to lessen the friction between the femoral component 20, which is metallic, and the tibial component 25, and thus result in a more natural operation of the total knee prosthesis 19. A keel 28 projects downwardly from the metallic part 27a and is used for securing the tibial component 25 in the intermedullary canal of the tibia bone 3, as shown in FIG. 7.

Figure 7:
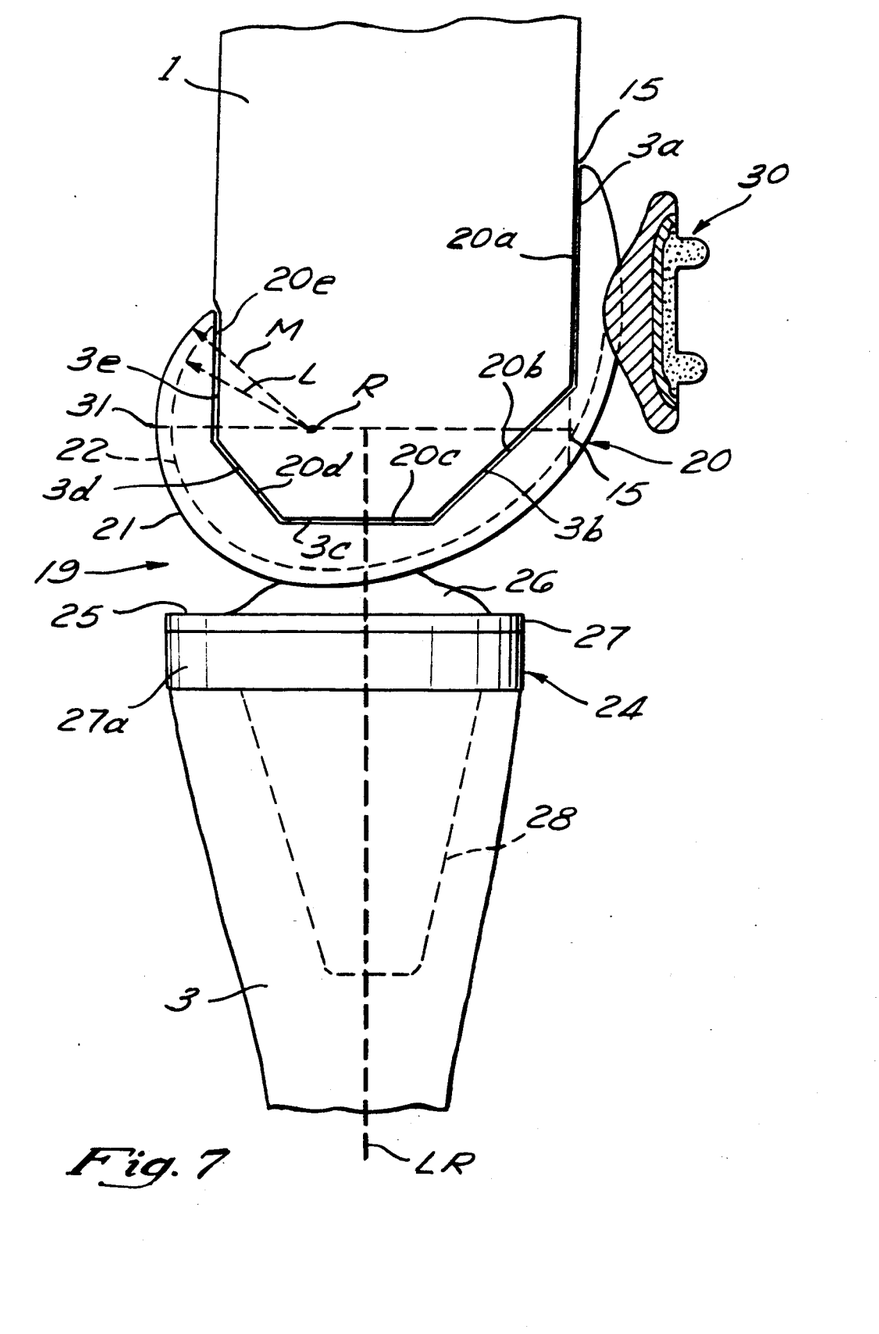
FIG. 7 is a side view of total knee endoprosthesis with an optional patellar component.

FIG. 7 is a side view of the total knee endoprosthesis 19 for the left knee with a patellar component 30 which slidably engages with the patellar groove 23 of the anterior portion of the femoral component 20. The total knee endoprosthesis 19 is shown affixed to the femur bone 1 and the tibia bone 3. In order to fix the total knee endoprosthesis 19 in the body, the distal end of the femur bone 3 is sawn off to have flats 3a, b, c, d, and e which will engage with the corresponding inside flat surfaces 20a, b, c, d, and e of the femoral implant component 20. The femoral component 20 is then affixed to the distal end of the femur by conventional means, such as by cement, pegs and the like (not shown). The medially facing surface of the medial condyle and the laterally facing surface of the lateral condyle of the anatomical femur are left intact with the medial collateral ligaments (MCL) and the lateral collateral ligaments (LCL) left attached at their origins on the femur (not shown). Thus, the MCL and LCL will provide the necessary anchoring support which holds the femoral portion 20 and tibial portion 24 together. The proximal top of the tibia bone 3 is sawn off to receive the tibial component 24. The keel 28 will lodge in the intermedullary canal of the tibia 3 and is cemented in place atop the tibia 3. As shown in FIG. 7, in the total knee endoprosthesis 19, as in the anatomical knee, the posterior portions of the medial and lateral condyles 21 and 22 are generally circular in cross-section, when viewed through a plane perpendicular to the FE axis. The medial condyle 21 has a larger radius of curvature M (from point R to the outer perimeter of the medical condyle, taken through a plane perpendicular to the FE axis) than the radius of curvature L of the lateral condyle 22. The longitudinal axis of rotation (LR) of the tibia is likewise a fixed axis and is anterior and not perpendicular to FE axis. The offset of the FE axis from the transverse and coronal planes explains the observed valgus external rotation with extension for the knee and the varus internal rotation with flexion of the knee. When motion occurs about the fixed FE by flexion-extension of the knee axis and LR axis (by turning of the foot), which are non-orthogonal axes, the motion is pure rotation about these axes.

Figure 10:
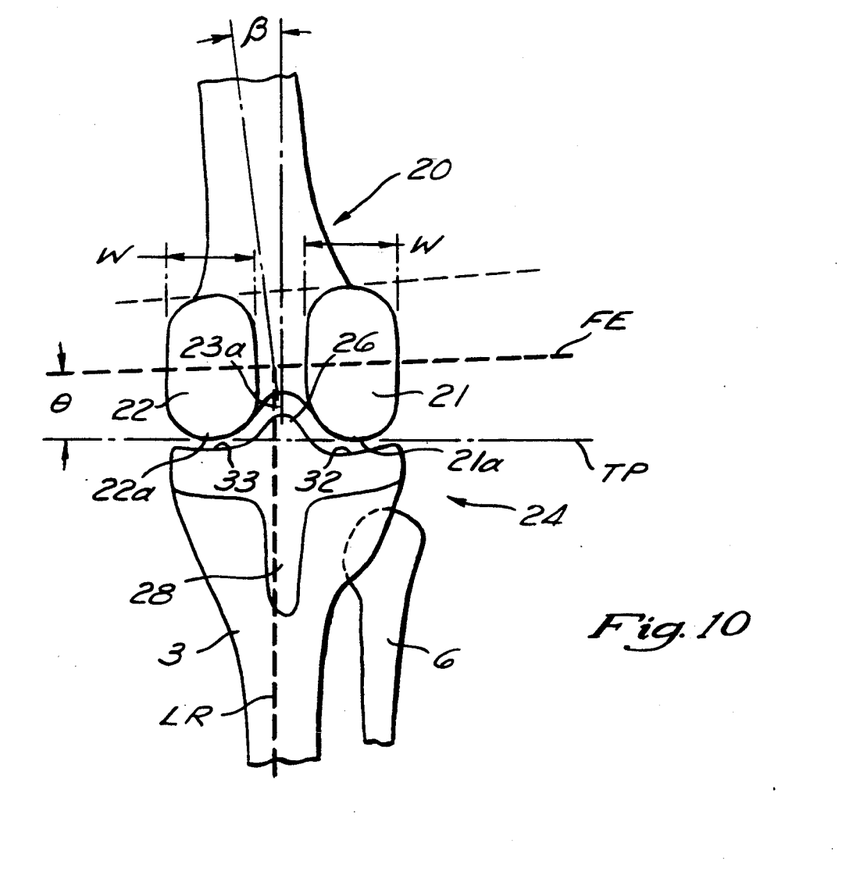
FIG. 10 is a posterior view of the femoral component of FIG. 9 fixed to the femur bone and the tibial component.

When the total knee prosthesis is installed, and the recipient is in a standing position with the endoprosthesis knee 19 in total extension, the distal most surfaces of the medial and lateral 21 and 22 slidably seat in the concavities such that the condyles are in the transverse (horizontal) plane (best shown in FIG. 10). In such a position, the FE axis, which passes a line which passes through the centers of curvature and rotation of the medial and lateral condyles, is directed inferiorly and posteriorly from the medial condyle 21 to the lateral condyle 22 by an angle $\theta$ and $\alpha$ of 3.0 to 3.8 degrees equally and respectively from the transverse and coronal planes TP and CP. The FE axis passes through the origins of the medial collateral ligaments (MCL) and lateral collateral ligaments (LCL) on the sides of the distal femur and is superior to the intersection of the cruciate ligaments. The LR axis passes through the insertion of the anterior cruciate ligament (ACL) on the tibial plateau and is directed postero-medially in the proximity of the insertion of the posterior cruciate ligament (PCL) at the femoral notch.

Figure 9:
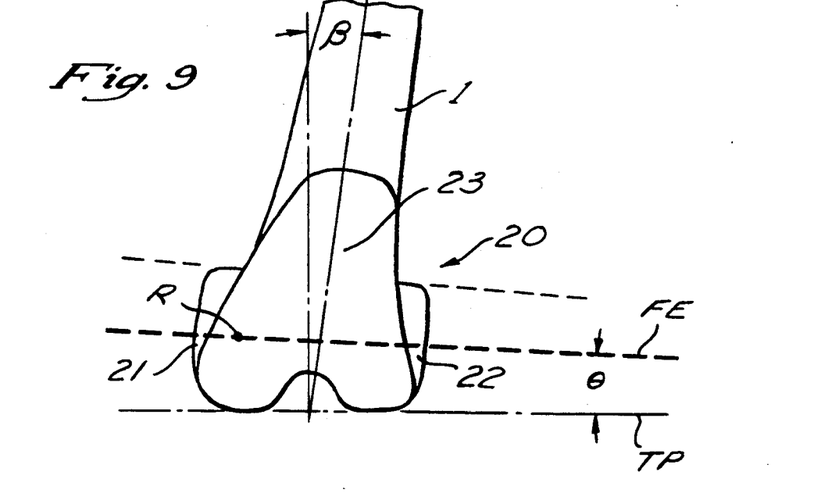
FIG. 9 is an anterior view of the femoral component of the prosthetic knee fixed to the femur bone

In the total knee endoprosthesis 19, the orientation of the FE axis also corresponds to an orientation in which the FE axis passes through the center of the medial condyle portion 21 at point R that is 35 percent ±5 percent of the distance from the posterior-most portion of the medial condyle 31 to the anterior projection of the femoral shaft 15, (which lies adjacent to the flat 20a of the femoral component), and is on the posterior side of the femoral portion. From that point, the FE axis is directed 3.0 to 3.8 degrees posteriorly and inferiorly from the medial condyle portion to the lateral condyle portion. As shown in FIG. 9, the patellar groove 23 is perpendicular to the FE axis. The tibial plateau 25 is sloped downwardly in the posterior direction at a slant of approximately 4 degrees. The radii of curvature of the posterior and distal portions of the medial condyle portion M and the posterior and distal portions of the lateral condyle portion L are circular through a sweep of over 120 degrees, and ideally a sweep of approximately 135 degrees. Thus, the natural movement of the anatomic knee is mimicked in the instant prosthetic knee.

Figure 8:
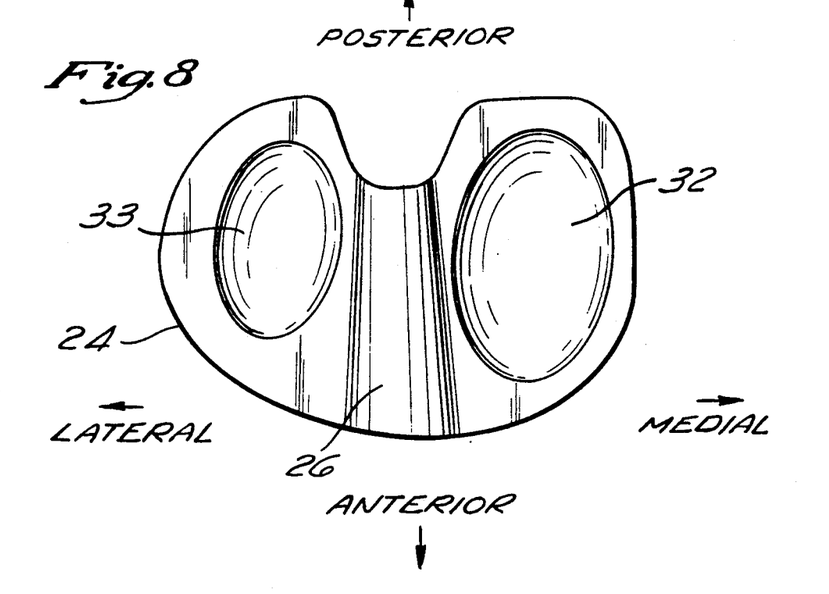
FIG. 8 is a top plan view of the tibial plateau of the tibial component.
Figure 8A:
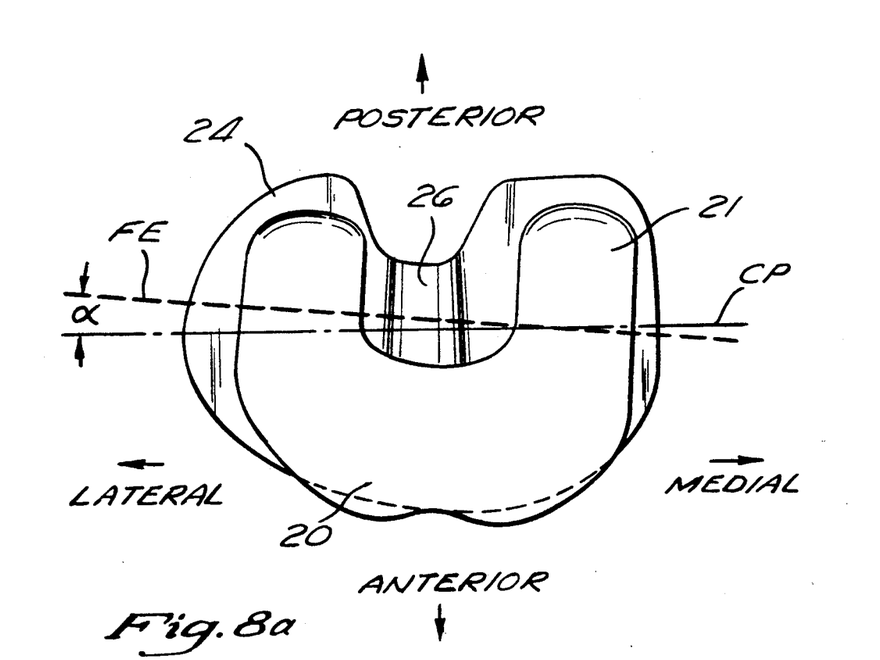
FIG. 8a is a top plan view of the outline of the femoral component seating on the tibial component to show the offset of the FE axis from the coronal plane.

FIG. 8 is a top plan view of the tibial component 24. The medial concavity 32 is larger and deeper than the lateral concavity 33 and the two concavities are divided by a the raised eminence 26. The eminence 26 slides between the groove 23a between the medial and lateral condyle portions 21 and 22. The eminence 26 is sized in relationship to the two condyles and their spacing so that the tibia bone 3 and its associated tibial component 24 will be allowed to rotate by approximately 15 to 30 degrees about the LR axis, yet not be separated from each other. The raised eminence 26 is ideally taller posteriorly than anteriorly. The anterior part of the raised eminence 26 will act as a stop to prevent the tibial component 24 from moving too far forward on the femoral component 20, and thus prevents over-flexion of the prosthetic knee, much in the same way found in the anatomical knee. FIG. 8a shows the posterior offset of the FE axis from the coronal plane CP by angle $\alpha$ of 3.0 and 3.8 degrees directed from medial to lateral.

FIG. 9 is a front view of the left femoral component 20 affixed to the femur 1. The distal most surface of the medial and lateral condyle portions 21 and 22 are in the transverse (horizontal) plane TP. The FE axis is directed inferiorly (downwardly) from the medial condyle 21 to lateral condyle 22 by an angle $\theta$ of 3.0 to 3.8 degrees. Also, the femoral component 20 is offset from the sagittal plane by an angle $\beta$ ranging between 3 to 7 degrees to compensate for the normal valgus offset of the femur bone. Practically, the angle $\beta$ can be selected as 3 degrees, 5 degrees, and 7 degrees to provide for the typical valgus offsets found in the body.

FIG. 10 is a rear view of the femoral component 20 affixed to the femur bone 21 and shows its contact with the tibial component 24. As is readily apparent from FIGS. 9 and 11, the medial and lateral condyle portions 21 and 22 have equal width W and are curved at their distal most portions 21a and 22a to slideably fit in the medial and lateral concavities 32 and 33 on the tibial component 24. The raised eminence 26 slides in the groove 23a between the medial and lateral condyles 21 and 22 and prevents the femoral and tibial components 20 and 24 from becoming separated, as well as the other functions discussed above.

The femoral component 20 can be fashioned from stainless steel, titanium, chrome-molybdenum alloys, or other applicable materials.

Figure 11:
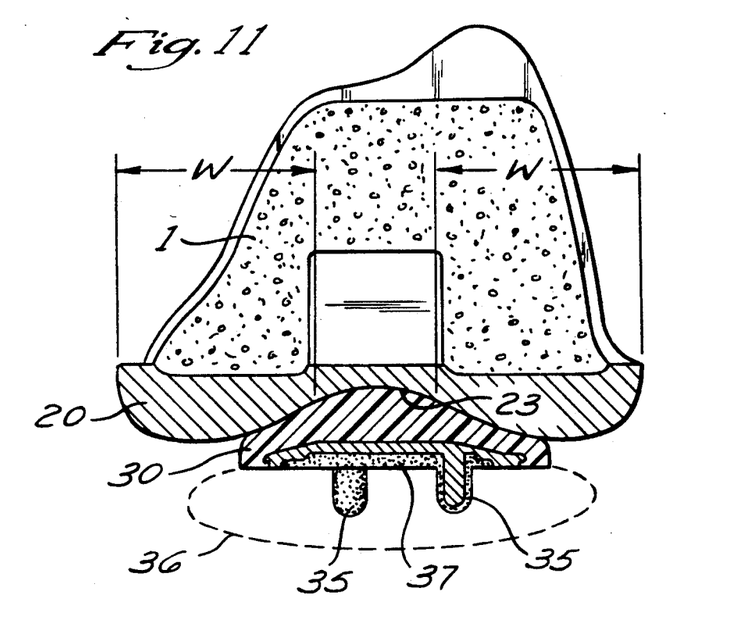
FIG. 11 is a partial cross-sectional view of the prothesis in the transverse plane through the optional patellar component and femoral component showing the interface between the two.
Figure 12:
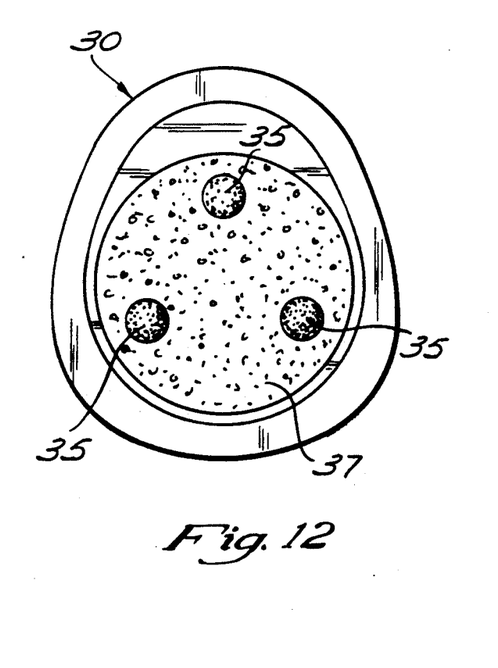
FIG. 12 is an anterior view of the optional patellar component.
Figure 13:
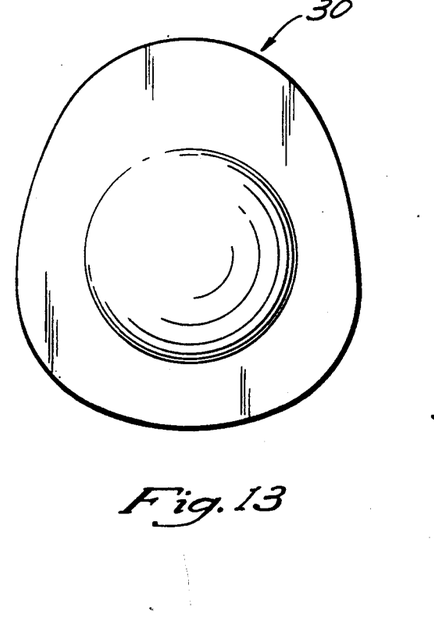
FIG. 13 is a posterior view of the optional patellar component.

FIG. 11 is a partial cross-sectional view showing the interface between the femoral component 20, the femur bone 1, and the optional patellar component 30 which slides in the patellar groove 23. As shown in FIGS. 11 and 12, pegs 35 can be used to affix the patellar component 30 to the remaining part of the patella 36 (shown in phantom lines). FIG. 12 is a rear view of the patellar component 30 showing the curvature of its patellar groove facing surface thereof which allows it to slide in the patellar groove 23. The front of the patellar component 37 ideally has a rough surface to aid cement adhesion of the patellar component 30 to the patella 36. The patellar component 30 is optional and may be excluded in the event the anatomical patella is healthy and undamaged and available to for use with the total knee prosthesis 20. Ideally, the patellar component 30 is made of plastic material, at least where it makes contact with the patellar groove 23.

Although the total knee endoprosthesis shown in the Figures is for the left knee the description of the knee is equally applicable for the right knee when considering the anatomical planes.

Due to the fact that the FE axis passes through the centers of curvature of the medial and lateral condyle portions, which also pass through the origins of the medial collateral ligaments (MCL) and the lateral collateral ligaments (LCL) (which remain on the exterior surface of the condyles after the femur is sawn to form the mating surfaces for the femoral component), the stresses put on the endoprosthetic knee by the collateral ligaments at all positions of extension and flexion closely mimic that of the anatomical knee.

In the prior art knee prosthetic devices, due to a non-fixed FE axis, the collateral ligaments are unnaturally stressed because the tension put on these ligaments will vary depending on the changing orientation of the femur and tibia bones to each other. These increased tensions and stresses which the ligaments are made to bear, which are frequently weak and deteriorated to begin with, not only often lead to their further deterioration and failure, but also put additional stress on the prosthetic knee joints, leading to detachment and/or cracking. It is thus evident that Applicant's total knee endoprosthesis is far superior to the prior art prosthetic knee joints.

The drawings and the foregoing description are not intended to represent the only form of the invention in regard to the details of its construction and manner of operation. In fact, it will be evident to one skilled in the art that modifications and variations may be made without departing from the spirit and scope of the invention. Changes in form and in the proportion of parts, as well as the substitution of equivalents, are contemplated as circumstances may suggest or render expedient; and although specific terms have been employed, they are intended in a generic and descriptive sense only and not for the purpose of limitation, the scope of the invention being delineated in the following claims:

I claim:

1. A total knee endoprosthesis having a fixed flexion-extension axis of rotation for implantation in a patient's body, comprising:

a femoral implant component for connection to the distal end of the recipient's femur bone, said femoral implant component having a medial condyle portion and a lateral condyle portion, said medial condyle and lateral condyle portions being spaced apart at their posterior and distal portions and having a patellar groove located at least partially therebetween on an anterior position of said femoral implant component, said medial condyle portion being larger than said lateral condyle portion, said posterior and distal portions of said condyles being circular in cross-section through a sweep of over 120 degrees and having a non-moving center of rotation; and a tibial implant component for connection to the proximal end of the patient's tibia bone, said tibial implant component having a plateau surface facing said femoral implant component, said plateau surface having a medial and lateral concavity defined thereon, said medial concavity being larger than said lateral concavity, said two concavities being separated by a raised eminence which slides between said spaced apart medial and lateral condyle portions;

wherein when said total knee endoprosthesis is implanted in the recipient's body, a fixed flexion-extension axis passes through the center of rotation of said medial and lateral condyle portions, said flexion-extension axis being oriented posteriorly and inferiorly from said medial condyle portion to said lateral condyle portion by 3.0 to 3.8 degrees from both the transverse and coronal planes, and whereby said patellar groove is perpendicular to said flexion-extension axis.

2. The total knee endoprosthesis of claim 1, wherein said medial and lateral condyle portions have equal width.

3. The total knee endoprosthesis of claim 1, wherein said femoral component is fixed to the femur bone with a three to seven degree valgus offset of the distal most portion of the condyle to the intermedullary canal of the femur bone.

4. The total knee endoprosthesis of claim 1, wherein said tibial plateau surface is sloped posteriorly by approximately four degrees.

5. The total knee endoprosthesis of claim 1, wherein said tibial implant component and its associated tibia bone can rotate in the range of 15 to 30 degrees relative to the femoral component along a longitudinal rotation axis which is nonorthogonal and anterior said fixed flexion-extension axis.

6. The total knee endoprosthesis of claim 1, wherein said medial and lateral condyle portions are circular in their posterior and distal portions through a sweep of approximately 135 degrees.

7. The total knee endoprosthesis of claim 1, wherein the flexion-extension axis passes through a point in the center of the medial condyle portion through the sagittal plane which is 35 percent of the distance from the posterior-most portion of said medial condyle portion to the anterior projection of the femoral shaft which fits tightly against a backside of the anterior-most portion of the femoral component, said flexion-extension axis being directed posteriorly and inferiorly therethrough to said lateral condyle portion equally by an angle ranging from 3.0 to 3.8 degrees.

8. The total knee endoprosthesis of claim 1, wherein the flexion-extension axis passes through the origins of medial and lateral collateral ligaments.

9. The total knee endoprosthesis of claim 1, wherein said flexion-extension axis passes through the center of said medial condyle portion at a point that is 35 percent ±5 percent of the distance from the posterior-most point of the medial condyle to the anterior projection of the femoral shaft and is on the posterior side of the femoral portion and is directed 3.0 to 3.8 degrees posteriorly and inferiorly from said medial condyle portion to said lateral condyle portion.

10. The total knee endoprosthesis of claim 1, wherein said tibial implant component has a keel under said plateau surface for fixation to the tibia bone.

11. The total knee endoprosthesis of claim 1, wherein said raised eminence on said tibial plateau is taller on its posterior side than its anterior side.

12. The total knee endoprosthesis of claim 1, further comprising a patellar component which slides in said patellar groove and which is affixed to the posterior surface of the anatomical patella.

13. The total knee endoprosthesis of claim 1, wherein said medial and lateral concavities in said tibial implant component are deepest midpoint between the front and rear of the tibial implant component.

14. A total knee endoprosthesis, having a fixed and non-moving flexion-extension axis of rotation, for implantation in a patient's body, comprising:

a femoral implant component for permanent affixation to the distal end of the patient's femur bone, said femoral implant component having spaced apart medial and lateral condyle portions, posterior and distal portions of said condyle portions being generally circular as viewed in a plane perpendicular to said flexion-extension axis and having non-moving centers of rotation in said generally circular posterior and distal condyle portions, said medial condyle portion being larger than said lateral condyle portion; and a tibial implant component for connection to the proximal end of the patient's tibia bone, said tibial implant component having a plateus surface facing said femoral implant component, said plateau surface having a medial and lateral concavity defined thereon, said two concavities being separated by a raised eminence, wherein when said total knee endoprosthesis is implanted in the recipient's body, said fixed flexion-extension axis passes through the non-moving centers of rotation of said generally circular posterior and distal condyle portions, said flexion-extension axis thus being oriented posteriorly and inferiorly commencing from said medial condyle portion and extending to said lateral condyle portion along a line that is approximately 3.0 to 3.8 degrees from both the transverse and coronal planes.

15. The total knee endoprosthesis of claim 14, wherein said medial and lateral condyle portions have a patellar groove located therebetween on an anterior portion of said femoral implant component, and said medial concavity is larger than said lateral concavity on said tibial implant component.

16. The total knee endoprosthesis of claim 15, wherein said patellar groove is generally perpendicular to said flexion-extension axis.

17. The total knee endoprosthesis of claim 14, wherein said medial and lateral condyle portions have equal width as viewed in a coronal plane.

18. The total knee endoprosthesis of claim 14, wherein said medial and lateral condyle portions are generally circular in their posterior and distal portions through a sweep of approximately 135 degrees.

19. The total knee endoprosthesis of claim 14, wherein the flexion-extension axis passes through the origins of medial and lateral collateral ligaments.

20. The total knee endoprosthesis of claim 14, wherein said flexion-extension axis passes through a point in the medial condyle portion which is on an imaginary line spanning the distance from the posterior-most point of the medial condyle portion to the anterior projection of the femoral shaft, said point lying 35 percent ±5 percent of said distance measured from said posterior-most point of the medial condyle portion.

* * * * *